United States Patent [19]

Briner

[11] Patent Number: 5,047,426

[45] Date of Patent: Sep. 10, 1991

[54] FUNGICIDAL COMPOSITIONS

[75] Inventor: Paul H. Briner, Canterbury, England

[73] Assignee: Shell Internationale Research Maatschappij B.V., Netherlands

[21] Appl. No.: 397,756

[22] Filed: Aug. 23, 1989

[30] Foreign Application Priority Data

| Aug. 31, 1988 | [GB] | United Kingdom | 8820597 |
| Aug. 31, 1988 | [GB] | United Kingdom | 8820598 |
| Aug. 31, 1988 | [GB] | United Kingdom | 8820599 |
| Aug. 31, 1988 | [GB] | United Kingdom | 8820600 |
| Aug. 31, 1988 | [GB] | United Kingdom | 8820601 |
| Aug. 31, 1988 | [GB] | United Kingdom | 8820602 |

[51] Int. Cl.$^5$ .................. A61K 31/215; C07C 69/74; C07C 61/20

[52] U.S. Cl. .................. 514/530; 514/422; 514/523; 514/524; 514/525; 558/411; 558/412; 558/414; 558/415; 558/416; 558/417; 558/418; 558/421; 558/425; 560/128; 562/510

[58] Field of Search ............... 562/510; 514/573, 530, 514/522, 523, 524, 525; 560/128; 558/411, 412, 414, 415, 416, 417, 418, 421, 425

[56] References Cited

FOREIGN PATENT DOCUMENTS 1084390 1/1955 France .

OTHER PUBLICATIONS

Tsuboi et al., "A Michael Addition . . .", Bull. Chem. Soc. Jpn. 60, 836-838 (1987).

Fieser and Fieser, "Reagents for Organic Synthesis", John Wiley & Sons, 1974, p. 457.
Bull. Chem. Soc. Jap., 43(7), (1970), pp. 2204-2208.
Chem. Abs. 62, (1965), p. 2728.
Chem. Abs. 52: 13701i (1958).

Primary Examiner—C. Warren Ivy
Assistant Examiner—Celia Chang

[57] ABSTRACT

The invention provides fungicidal compositions which comprise a carrier and, as active ingredient, a compound of the general formula

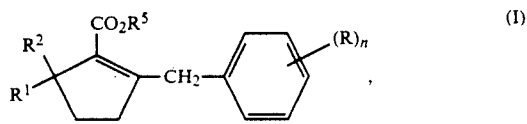

(I)

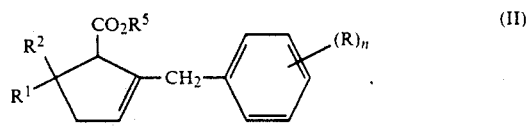

(II)

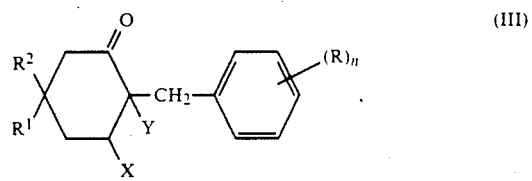

(III)

6 Claims, No Drawings

FUNGICIDAL COMPOSITIONS

This invention relates to fungicidal compositions containing cyclopentene, cyclohexanone and cyclohexenone derivatives, some of which are novel, a process for preparing such compounds and their use as fungicides.

Bull. Chem. Soc. Jap., 43,(7), (1970), pp. 2204-8 discloses 1-benzyl-2-carboxylcyclpent-1-ene and Bull. Chem. Soc. Jap., 60(2), pp. 836-8 discloses 1-benzyl-2-methoxycarbonylcyclopent-1-ene. However, there is no indication in these references that either of these compounds exhibits any fungicidal activity.

Chem. Abs. 62, (1965), p. 2728 discloses 2-(4-chlorobenzyl)dihydroresorcinol and 2-(4-bromobenzyl)dihydroresorcinol. However, this abstract gives no that either of these compounds exhibits significant fungicidal activity against phytopathogenic fungi.

Moreover, Chem. Abs. 52: 13701i (1958) discloses 2-benzyl-3-ethoxy-5,5-dimethylcyclohex-2-en-1-one but, again, there is no indication that this compound has any fungicidal properties.

It has now been found that certain cyclopentene, cyclohexanone and cyclohexenone derivatives exhibit fungicidal activity in specific screens.

According to the present invention there is therefore provided a fungicidal composition which comprises a carrier and, as active ingredient, a compound of the general formula

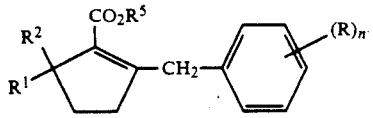

in which n represents an integer from 0 to 5; each R represents a halogen atom, nitro, cyano, hydroxyl, alkyl, haloalkyl, alkoxy, haloalkoxy, amino, alkylamino, dialkylamino, alkoxycarbonyl, carboxyl, alkanoyl, alkylthio, alkylsulphinyl, alkylsulphonyl, carbamoyl, alkylamido, cycloalkyl or phenyl group; $R^1$ and $R^2$ independently represent a hydrogen atom or an alkyl group; and $R^5$ represents a hydrogen atom or an alkyl or cycloalkyl group.

Also according to the present invention there is provided a fungicidal composition which comprises a carrier and, as active ingredient, a compound of the general formula

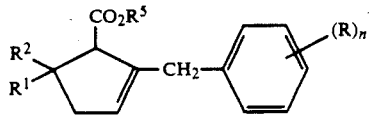

in which n, R, $R^1$, $R^2$ and $R^5$ are as defined above.

Further according to the present invention there is provided a fungicidal composition which comprises a carrier and, as active ingredient, a compound of the general formula

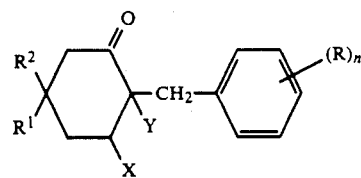

in which n, R, $R^1$ and $R^2$ are as defined above and X and Y independently represent a halogen atom.

According to another aspect of the present invention there is provided a compound of the general formula

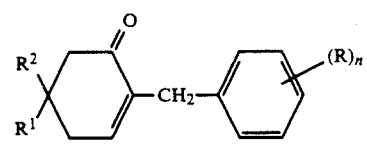

in which n, R, $R^1$ and $R^2$ are defined above.

According to a further aspect of the present invention there is provided a fungicidal composition which comprises a carrier and, as active ingredient, a compound of the general formula

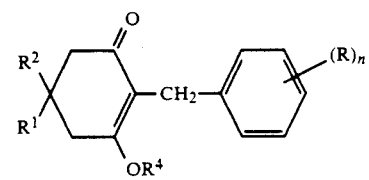

in which n, R, $R^1$ and $R^2$ are defined above and $R^4$ represents an alkyl group.

When any of the foregoing substituents represents or contains an alkyl substituent groups, this may be linear or branched and may contain up to 12, preferably up to 6, and especially up to 4, carbon atoms. A cycloalkyl substituent group may contain 3 to 8, preferably 3 to 6, carbon atoms.

It is preferred that $R^1$ and $R^2$ independently represent a hydrogen atom or a $C_{1-4}$alkyl, particularly a methyl, group.

Preferably, R represents a halogen, especially a chlorine, atom.

It is also preferred that $R^5$ represents a hydrogen atom or a $C_{1-6}$alkyl group Most preferably, $R^5$ represents a methyl group.

It is also preferred that $R^4$ represents a primary or secondary alkyl group, primary alkyl groups being especially preferred. Preferably, $R^4$ represents a $C_{1-4}$alkyl group, especially a primary $C_{1-4}$alkyl group. Most preferably, $R^4$ represents a methyl or butyl, especially an isobutyl, group.

It is further preferred that X and Y independently represent a chlorine or bromine atom. Most preferably, X and Y both represent a bromine atom.

A particularly preferred sub-group of compounds of formulae I, II, III, VI and VII is that in which n is 1, R represents a chlorine atom, preferably substituted at the 4-position of the phenyl ring, $R^1$ and $R^2$ both represent a hydrogen atom or both represent a methyl group.

A method of making fungicidal compositions according to the invention is also provided which comprises bringing a compound of formula I, II, III, VI or VII into association with at least one carrier Such compositions may contain a single compound or a mixture of several compounds of formulae I, II, III, VI or VII.

A composition according to the invention preferably contains from 0.5 to 95% by weight of active ingredient.

A carrier, in a composition according to the invention is any material with which the active ingredient is formulated to facilitate application to the locus to be treated, which may for example be a plant, seed or soil, or to facilitate storage, transport or handling. A carrier may be a solid or a liquid, including a material which is normally gaseous but which has been compressed to form a liquid, and any of the carriers normally used in formulating fungicidal compositions may be used.

Suitable solid carriers include natural and synthetic clays and silicates, for example natural silicas such as diatomaceous earths; magnesium silicates, for example talcs; magnesium aluminum silicates, for example attapulgites and vermiculites; aluminum silicates, for example kaolinites, montmorillonites and micas; calcium carbonate; calcium sulphate; ammonium sulphate; synthetic hydrated silicon oxides and synthetic calcium or aluminum silicates; elements, for example carbon and sulphur; natural and synthetic resins, for example coumarone resins, polyvinyl chloride, and styrene polymers and copolymers; solid polychlorophenols; bitumen; waxes, for example beeswax, paraffin wax, and chlorinated mineral waxes; and solid fertilizers, for example superphosphates.

Suitable liquid carriers include water; alcohols, for example isopropanol and glycols; ketones, for example acetone, methyl ethyl ketone, methyl isobutyl ketone and cyclohexanone; ethers; aromatic or araliphatic hydrocarbons, for example benzene, toluene and xylene; petroleum fractions, for example kerosine and light mineral oils; chlorinated hydrocarbons, for example carbon tetrachloride, perchloroethylene and trichloroethane. Mixtures of different liquids are often suitable.

Fungicidal compositions are often formulated and transported in a concentrated form which is subsequently diluted by the user before application. The presence of small amounts of a carrier which is a surface-active agent facilitates this process of dilution. Thus preferably at least one carrier in a composition according to the invention is a surface-active agent. For example the composition may contain at least two carriers, at least one of which is a surface-active agent.

A surface-active agent may be an emulsifying agent, a dispersing agent or a wetting agent; it may be nonionic or ionic. Examples of suitable surface-active agents include the sodium or calcium salts of polyacrylic acids and lignin sulphonic acids; the condensation products of fatty acids or aliphatic amines or amides containing at least 12 carbon atoms in the molecule with ethylene oxide and/or propylene oxide; fatty acid esters of glycerol, sorbitol, sucrose or pentaerythritol; condensates of these with ethylene oxide and/or propylene oxide; condensation products of fatty alcohol or alkyl phenols, for example p-octylphenol or p-octylcresol, with ethylene oxide and/or propylene oxide; sulphates or sulphonates of these condensation products; alkali or alkaline earth metal salts, preferably sodium salts, of sulphuric or sulphonic acid esters containing at least 10 carbon atoms in the molecule, for example sodium lauryl sulphate, sodium secondary alkyl sulphates, sodium salts of sulphonated castor oil, and sodium alkylaryl sulphonates such as dodecylbenzene sulphonate; and polymers of ethylene oxide and copolymers of ethylene oxide and propylene oxide.

The compositions of the invention may for example be formulated as wettable powders, dusts, granules, solutions, emulsifiable concentrates, emulsions, suspension concentrates and aerosols. Wettable powders usually contain 25, 50 or 75% w of active ingredient and usually contain in addition to solid inert carrier, 3-10% w of a dispersing agent and, where necessary, 0-10% w of stabilizer(s) and/or other additives such as penetrants or stickers. Dusts are usually formulated as a dust concentrate having a similar composition to that of a wettable powder but without a dispersant, and may be diluted in the field with further solid carrier to give a composition usually containing ½-10% w of active ingredient. Granules are usually prepared to have a size between 10 and 100 BS mesh (1.676–0.152 mm), and may be manufactured by agglomeration or impregnation techniques. Generally, granules will contain ½-75% w active ingredient and 0-10% w of additives such as stabilizers, surfactants, slow release modifiers and binding agents. The so-called "dry flowable powders" consist of relatively small granules having a relatively high concentration of active ingredient. Emulsifiable concentrates usually contain, in addition to a solvent and, when necessary, co-solvent, 1-50% w/v active ingredient, 2-20% w/v emulsifiers and 0-20% w/v of other additives such as stabilizers, penetrants and corrosion inhibitors. Suspension concentrates are usually compounded so as to obtain a stable, non-sedimenting flowable product and usually contain 10-75% w active ingredient, 0.5-15% w of dispersing agents, 0.1-10% w of suspending agents such as protective colloids and thixotropic agents, 0-10% w of other additives such as defoamers, corrosion inhibitors, stabilizers, penetrants and stickers, and water or an organic liquid in which the active ingredient is substantially insoluble; certain organic solids or inorganic salts may be present dissolved in the formulation to assist in preventing sedimentation or as antifreeze agents for water.

Aqueous dispersions and emulsions, for example compositions obtained by diluting a wettable powder or a concentrate according to the invention with water, also lie within the scope of the invention. The said emulsions may be of the water-in-oil or of the oil-in-water type, and may have a thick 'mayonnaise' like consistency.

The composition of the invention may also contain other ingredients, for example other compounds possessing herbicidal, insecticidal or fungicidal properties.

Of particular interest in enhancing the duration of the protective activity of the compounds of this invention is the use of a carrier which will provide a slow release of the fungicidal compounds into the environment of the plant which is to be protected. Such slow-release formulations could, for example, be inserted in the soil adjacent to the roots of a plant, or could include an adhesive component enabling them to be applied directly to the stem of a plant.

According to the present invention there is also provided a compound of the general formula II, III or VI in which n, R, $R^1$, $R^2$, $R^5$, X and Y are as defined above.

According to another aspect of the present invention there is provided a compound of the general formula I in which n, R, $R^1$, $R^2$ and $R^5$ are as defined above with the proviso that, when n is 0 and $R^1$ and $R^2$ both represent a hydrogen atom, $R^5$ does not represent a hydrogen atom or a methyl group.

According to a further aspect of the present invention there is provided a compound of the general formula VII in which n, R, $R^1$, $R^2$ and $R^4$ are as first defined above with the provisos that, when n is 1, $R^1$ and $R^2$ both represent a hydrogen atom and $R^4$ represents a methyl group then R does not represent a chlorine or bromine atom substituted at the 4-position of the phenyl ring, and, when n is 0 and $R^1$ and $R^2$ both represent a methyl group, $R^4$ does not represent an ethyl group.

The invention still further provides the use as a fungicide of a composition as defined above or a compound of formula I, II, III, VI or VII as defined above, and a method for combating fungus at a locus, which comprises treating the locus, which may be for example plants subject to or subjected to fungal attack, seeds of such plants or the medium in which such plants are growing or are to be grown, with such a compound or composition.

The present invention also provides a process for the preparation of a compound of formula I as defined above which comprises heating a compound of the general formula

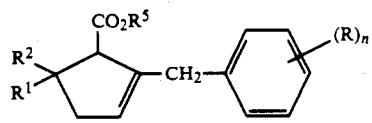

or the general formula

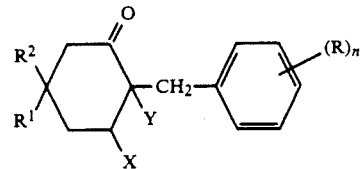

n, R, $R^1$, $R^2$ and $R^5$ are as first defined above with the proviso that, when n is 0 and $R^1$ and $R^2$ both represent a hydrogen atom, $R^5$ does not represent a hydrogen atom or a methyl group, and X and Y are as defined above with a compound of the general formula

MOR$^5$ (IV)

in which $R^5$ is as first defined above and M represents an alkali metal, preferably a sodium, atom, in the presence of a polar solvent.

Preferably, the polar solvent is a compound of the general formula

R$^5$OH (V)

in which $R^5$ is as first defined above, dimethylformamide or dimethylsulphoxide.

If a compound of formula V is used as solvent, preferably, $R^5$ has the same meaning in formula IV and formula V. For instance, if the compound of formula IV is sodium methoxide, it is preferred that the solvent of formula V is methanol.

The reaction is conveniently carried out at a temperature from 80° C. to the reflux temperature of the solvent. Preferably, an excess of the compound of formula IV is used.

The present invention further provides a process for the preparation of a compound of formula II as defined above which comprises reacting a compound of the general formula

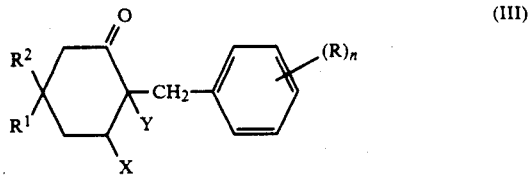

in which n, R, $R^1$ and $R^2$ are as first defined above and X and Y are as defined above with a compound of the general formula

MOR$^5$ (IV)

in which $R^5$ is as first defined above and M is as defined above in the presence of a solvent of the general formula

R$^5$OH (V)

in which $R^5$ is as first defined above.

Preferably, $R^5$ has the same meaning in formula IV and formula V. For instance, if the compound of formula IV is sodium methoxide, it is preferred that the solvent of formula V is methanol.

The reaction is conveniently carried out at a temperature from 0° C. to the reflux temperature of the solvent V, preferably, using an excess of the compound of formula IV.

The present invention still further provides a process for the preparation of a compound of formula III as defined above which comprises reacting a compound of the general formula

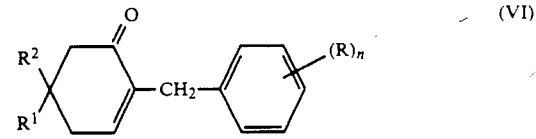

in which n, R, $R^1$ and $R^2$ are as first defined above, with a compound XY, in which X and Y are as defined above. Alternatively, compounds of formula III may be generated in situ and then treated with a compound of formula IV as described above to form compounds of formula I in a one-pot synthesis.

The process may be carried out in the presence of a solvent. Suitable solvents include petroleum, lower alcohols, such as methanol, chlorinated hydrocarbons, such as carbon tetrachloride, ethers and acetic acid.

The reaction is suitably carried out at a temperature from −10° C. to room temperature, depending on the nature of the solvent, if present. The preferred temperature is from 0° C. to room temperature.

The present invention also provides a process for the preparation of a compound of formula VI as defined above which comprises reacting a compound of the general formula

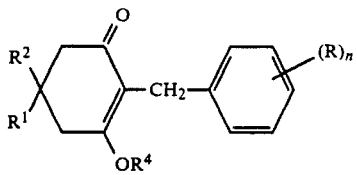

in which N, R, $R^1$, $R^2$ and $R^4$ are as first defined above, with a reducing agent and subsequently hydrolysing the reaction mixture.

The reducing agent is preferably a strong reducing agent, such as a complex metal hydride or hydrogen in combination with a catalyst. Complex metal hydrides, such as lithium aluminum hydride, sodium aluminum hydride and modified derivatives thereof such as "REDAL" (Trade Mark: sodium bis (2-methoxyethoxy) aluminum hydride in toluene), are especially preferred.

The process is conveniently carried out in the presence of a solvent. Suitable solvents include ethers, such as diethyl ether, tetrahydrofuran and oligoethers, and hydrocarbons.

The reaction is suitably carried out at a temperature from 20° C. to 80° C., depending on the nature of the solvent, if present.

It is advisable to destroy any excess reducing agent remaining at the end of the reduction process to prevent further reaction. If a complex metal hydride, such as lithium aluminum hydride, is used as reducing agent, any excess may be destroyed by the addition of water and sodium hydroxide to the reaction mixture.

This process for preparing compounds of formula VI proceeds via an enol ether intermediate. Accordingly, to obtain compounds of formula VI, it is necessary to include a hydrolysis work-up in the above process. This may comprise the addition of a dilute mineral acid, such as hydrochloric acid, to the reaction mixture after the reduction step and serves to convert any remaining intermediate enol ether into the desired cyclohexenone derivative of formula VI.

The present invention further provides a process for the preparation of a compound of formula VII as defined above which comprises reacting a compound of the general formula

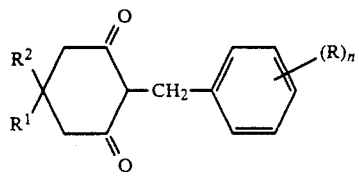

in which n, R, $R^1$ and $R^2$ are as first defined above, with a first compound of the general formula $R^4OH$ (IX)

in which $R^4$ is as first defined above, with the provisos that, when n is 1, $R^1$ and $R^2$ both represent a hydrogen atom and $R^4$ represents a methyl group then R does not represent a chlorine or bromine atom substituted at the 4-position of the phenyl ring, and, when n is 0 and $R^1$ and $R^2$ both represent a methyl group, $R^4$ does not represent an ethyl group, in the presence of an acid; and, if desired, converting the compound of formula VII so obtained into another compound of formula VII by reaction with a second different compound of formula IX in the presence of an acid.

The acid may be any substance which acts as a source of protons. Suitable acids include inorganic acids such as sulphuric acid, organic acids such as p-toluenesulphonic acid and ion exchange resins.

The process may be carried out in the presence of a solvent. Suitable solvents include petroleum, toluene and benzene. Solvents which form azeotropic mixtures with the reactants are particularly preferred.

The reaction is suitably carried out at a temperature from 70° C. to 130° C., depending on the nature of the solvent, if present. The preferred temperature is from 80° C. to 120° C.

Compounds of formula VIII may be conveniently prepared by reacting a compound of the general formula

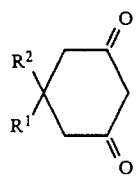

in which $R^1$ and $R^2$ are as first defined above, with a compound of the general formula

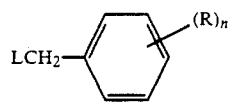

in which R and n are as first defined above and L represents a suitable leaving group, in the presence of a suitable base, such as potassium hydroxide.

Compounds of formula IV, V, IX, X and XI and the compounds XY are known compounds or can be prepared by processes analogous to known processes.

The compounds of formulae I, II, III, VI and VII are also useful as intermediates in the preparation of fungicidally active cyclopentane derivatives of the general formula

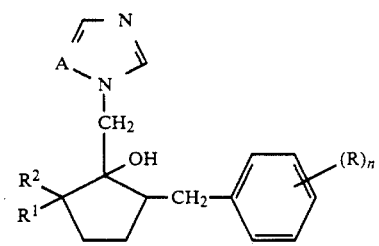

in which n, R, $R^1$ and $R^2$ are as first defined above and A represents a nitrogen atom or a CH group. Certain compounds of formula XII are the subject of co-pending patent applications GB-A1-2180236 and EP-A2-0267778.

The compounds disclosed in EP-A2-0267778 and GB-A1-2180236 exist in two stereoisomeric forms which have the following structures:

(XIIA)

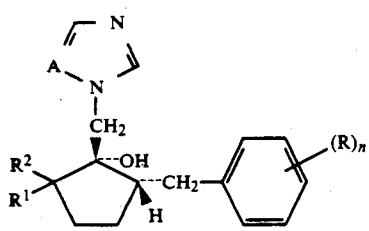

(XIIB)

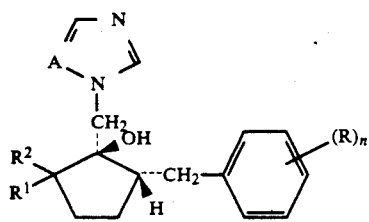

The letters A and B will be used hereinafter to denote compounds having the same stereochemical configuration as isomers A and B above.

Isomers A and B can be separated by, for instance, chromatography and exhibit different fungicidal activity. Generally, isomers of formula XIIA exhibit greater fungicidal activity than isomers of formula XIIB. The process used to synthesize compounds of formula XIIA from compounds of formulae I, II, III, VI and VII is set out in the following reaction scheme:

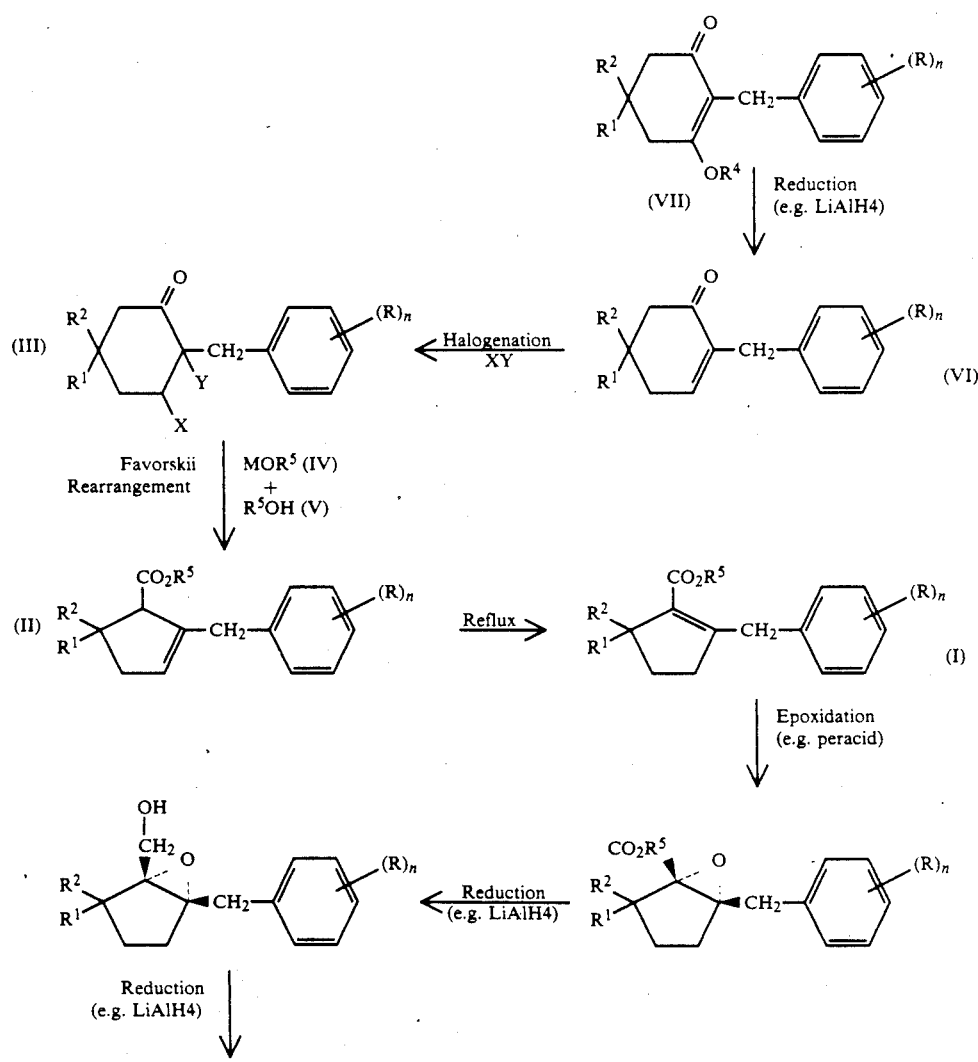

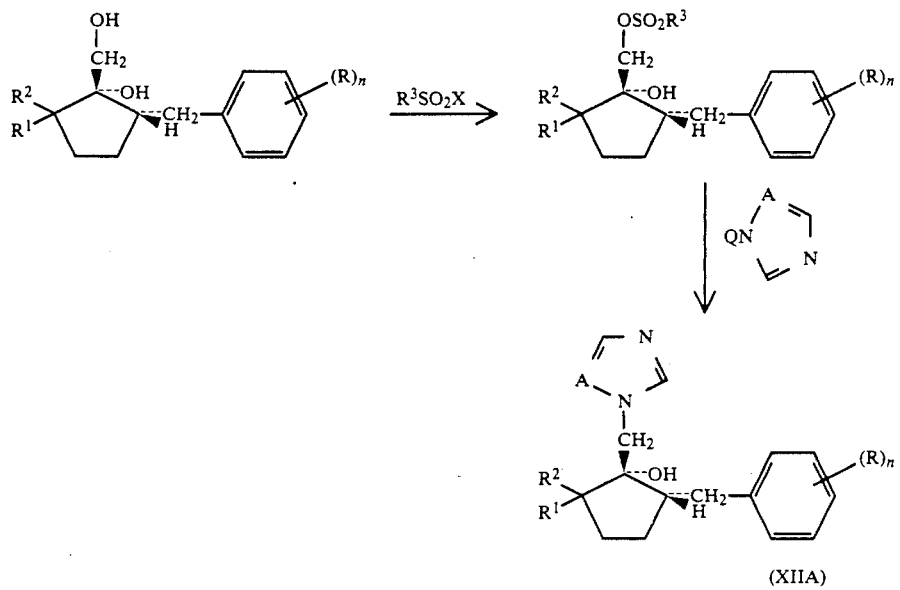

(XIIA)

In the above reaction scheme, n, R, $R^1$, $R^2$, $R^4$, $R^5$, X, Y, M and A are as previously defined, $R^3$ represents an optionally substituted alkyl or aryl group, preferably a $C_{1-4}$alkyl or a phenyl group each optionally substituted by one or more substituents selected from, halogen atoms, nitro, cyano, hydroxyl, $C_{1-4}$alkyl, $C_{1-4}$haloalkyl, $C_{1-4}$alkoxy, $C_{1-4}$haloalkoxy, amino, $C_{1-4}$alkylamino, di-$C_{1-4}$alkylamino, $C_{1-4}$alkoxycarbonyl, carboxyl, $C_{1-4}$alkanoyl, $C_{1-4}$alkylthio, $C_{1-4}$alkylsulphinyl, $C_{1-4}$alkylsulphonyl, carbamoyl, $C_{1-4}$alkylamido, $C_{3-8}$cycloalkyl and phenyl groups, and Q represents a hydrogen or alkali metal, preferably sodium, atom. The intermediate compounds and process steps in the above reaction scheme which are not part of the present invention are the subject of copending patent applications T 622, T 623, and T 626.

The invention is further illustrated by the following Examples.

EXAMPLE 1

Preparation of 2-(4-chlorobenzyl)-3-(2-methyl-propoxy)-5,5-dimethylcyclohex-2-en-1-one (Formula VII:n=1, R=4-Cl, $R^1$=$R^2$=$CH_3$, $R^4$=$(CH_3)_2$CH-$CH_2$O)

(a) Preparation of 2-(4-chlorobenzyl)-5,5-dimethyl-cyclohexane-1,3-dione 449 g (3.21 mols) dimedone (5,5-dimethylcyclohexane-1,3-dione) were added to a solution of aqueous potassium hydroxide comprising 166 g of 85% potassium hydroxide (2.52 moles) in 700 ml of water. The mixture was then warmed and a clear orange solution was obtained at 47° C. The solution was then heated to 59° C. and 544 g (3.21 mols) molten 4-chlorobenzyl chloride were added over a period of 1 hour with further heating to 85° C. Heating was continued for a further 2½ to 3 hours up to a temperature of 100° C. The mixture was then cooled, the solid product filtered off, washed with water and dried in a vacuum oven at 50° C. The crude solid (815 g) was then dissolved in 2400 ml methanol at reflux and 200 ml water added to produce a permanent cloudiness. The mixture was then allowed to cool to room temperature overnight with stirring.

The solid so obtained was filtered, washed with about 400 ml cold methanol and dried in a vacuum oven to produce 340 g 2-(4-chloro- benzyl)-5,5-dimethylcyclohexane-1,3-dione as a white solid, m.pt. 188°–190° C. Yield: 42%.

(b) Preparation of 2-(4-chlorobenzyl)-3-(2-methylpropoxy)-5,5-dimethylcyclohex-2-en-1-one 325 g (1.23 mol) of the 2-(4-chlorobenzyl)-5,5-dimethylcyclohexane-1,3-dione obtained in (a), 1.6 liters toluene, 182 g (2.5 mol) isobutanol and 5 g p-toluenesulphonic acid were stirred together at reflux under a Dean-Stark apparatus. The temperature of the reaction mixture was approximately 90° C. As water distilled off, the reaction mixture changed from a thin slurry to a yellow solution. After 14 hours reflux, the reaction mixture was cooled and shaken twice with 500 ml aliquots of 10% aqueous sodium hydroxide. The toluene layer was then flashed to give 389 g yellow/orange oil which crystallized on standing. Recrystallization of the solid from 60/80 petroleum produced 331 g 2-(4-chlorobenzyl)-3-(2- methylpropoxy)-5,5-dimethylcyclohex-2-en-1-one as a white crystalline solid, m.pt. 60°–61° C. Yield: 84%.

EXAMPLE 2

Preparation of 2

-(4

-chlorobenzyl)-3

-methoxy-5,5

- dimethylcyclohex-2

-en-1

-one (Formula VII: n=1,

R=4

-Cl, R$^1$

=R$^2$

=CH$_3$

O-)

A solution of 154 g of the 2-(4-chlorobenzyl)-3-(2-methylpropoxy)-5,5-dimethylcyclohex-2-en-1-one obtained in Example 1 in 1200 ml methanol containing 3 g p-toluenesulphonic acid was refluxed for 2 hours. The reaction mixture was then extracted with 3 liters water and 1 liter diethyl ether and re-extracted with a further 1 liter diethyl ether. The organic phases were then back-washed first with 200 ml 10% aqueous sodium hydroxide and then with 100 ml saturated sodium chloride solution, dried over anhydrous magnesium sulphate and flashed. The residue was then crystallized in 60/80 petroleum, filtered and air-dried to give 98 g 2-(4-chlorobenzyl)-3-methoxy-5,5-dimethylcyclohex-2-en-1-one as a white solid, m.pt 62°–63° C. Yield: 73%.

EXAMPLE 3

Preparation of 2

-(4

-chlorobenzyl)-5,5

-dimethyl- cyclohex-2

-en-1

-one (Formula VI: n=1,

R=4

-Cl, R$^1$

R$^2$

=CH$_3$)

98 g (0.35 mol) of the 2-(4-chlorobenzyl)-3-methoxy-5,5-dimethylcyclohex-2-en-1-one obtained in Example 2 were added to a slurry of 6.65 g (0.175 mol) lithium aluminum hydride in 490 mls diethyl ether at a rate sufficient to maintain reflux and the final reaction mixture refluxed for a further 30 minutes. 5 ml water were then added, followed by 5 ml 15% aqueous sodium hydroxide and a further 15 ml water and the resulting precipitate was filtered off. The filtrate was then shaken in 200 ml 5M hydrochloric acid for five minutes and the organic layer then separated, washed twice with 100 ml aliquots of saturated sodium bicarbonate solution, dried over anhydrous magnesium sulphate and stripped. The resulting oil was then dissolved in 430 mls dichloromethane, 18 g (0.085 mols) pyridinium chlorochromate were added and the reaction mixture stirred for 3 hours. 600 ml diethyl ether were added and the solid was then filtered off. The filtrate was washed three times with 10% sodium hydroxide, once with 2.5M hydrochloric acid and once with saturated sodium bicarbonate solution. It was then dried over anhydrous magnesium sulphate and stripped to give 82 g of crude product. Distillation of the crude product under reduced pressure (0.15 mm mercury) gave 79 g 2-(4-chlorobenzyl)-5,5-dimethylcyclohex-2-en-1-one, b.pt. 130° C. at 0.15 mm mercury. Yield: 91%.

EXAMPLE 4

Preparation of 2

-(4

-chlorobenzyl)-2,3

-dibromo-5,5

-dimethylcyclohexan-1

-one (Formula III: n=1,

R=4

-Cl, R$^1$

=R$^2$

=CH$_3$

, X=Y=Br)

10 g (40.2 mmols) of the 2-(4-chlorobenzyl)-5,5- dimethylcyclohex-2-en-1-one obtained in Example 3 were dissolved in 50 ml 30/40 petroleum at 0° C. 6.72 g (40.2 mmols) bromine were then added to the solution. After 5–10 minutes the solution decolourised and a precipitate formed. The solution was then cooled further and the precipitate filtered off to give 12.4 g 2-(4-chloro-benzyl)-2,3-dibromo-5,5-dimethyl- cyclohexan-1-one as a solid, m.pt. 82°–84° C. Yield: 75%.

EXAMPLE 5

Preparation of 1-(4-chlorobenzyl)-3,3-dimethyl-2-methoxycarbonylcyclopent-1-ene (Formula I: $n=1$, $R=4$-Cl, $R^1=R^2=CH_3$, $R^5=CH_3$)

A solution of sodium methoxide was prepared by adding 2.8 g (121 mmol) sodium to 50 ml methanol. A slurry of the 2-(4-chlorobenzyl)-2,3-dibromo-5,5- dimethylcyclohexan-1-one obtained in Example 4 in methanol was then prepared and added to the sodium methoxide solution at reflux. Reflux was continued overnight. The reaction mixture was then quenched with 200 ml water, extracted twice with 100 ml aliquots of diethyl ether, backwashed with water, dried over anhydrous magnesium sulphate and flashed to give 8 g of a yellow oil. By gas chromatography analysis, it was established that 6.6 g 1-(4-chlorobenzyl)-3,3-di- methyl-2-methoxycarbonyl-cyclopent-1-ene were produced as an oil. The structure of the product was established by n.m.r. spectroscopy. Yield: 78%.

EXAMPLE 6

Preparation of 2-(4-chlorobenzyl)-2,3-dibromo-5,5-dimethylcyclohexan-1-one (Formula III: $n=1$, $R=4$-Cl, $R^1=R^2=CH_3$, $X=Y=Br$)

5 g of the 2-(4-chlorobenzyl)-5,5-dimethylcyclo- hex-2-en-1-one obtained in Example 3 were dissolved in 25 ml tetrachloromethane at 5°–10° C. 3.2 g bromine were then added to the solution over a period of 10 minutes. The solution decolourised and 2-(4-chlorobenzyl)-2,3-dibromo-5,5-dimethylcyclohexa- n-1-one formed in solution

EXAMPLE 7

Preparation of 2-(4-chlorobenzyl)-4,4-dimethyl-3-methoxycarbonylcyclopent-1-ene (Formula II: $n=1$, $R=4$-Cl, $R^1=R^2=CH_3$, $R^5=CH_3$)

A solution of sodium methoxide was prepared by adding 1.1 g sodium to 10 ml methanol. 50 ml methanol was then added to the reaction mixture obtained in Example 6 followed by the solution of sodium methoxide, keeping the temperature of the reaction mixture at 10°–15° C. After 2 hours, the mixture was partitioned between dichloromethane and water, backwashed with water, dried over anhydrous magnesium sulphate and flashed to give 5.65 g crude 2-(4-chlorobenzyl)-4,4-dimethyl-3-methoxycarbonyl- cyclopent-1-ene as an oil. The structure of the product was established by n.m.r. spectroscopy.

EXAMPLE 8

Preparation of 1-(4-chlorobenzyl)-3,3-dimethyl-2-methoxycarbonylcyclopent-1-ene (Formula I: $n=1$, $R=4$-Cl, $R^1=R^2=CH_3$, $R^5=CH_3$)

The crude 2-(4-chlorobenzyl)-4,4-dimethyl-3- methoxycarbonylcyclopent-1-ene obtained in Example 7 was refluxed for 15 hours in methanol containing one equivalent of sodium methoxide to give 1-(4-chlorobenzyl)-3,3-dimethyl-2-methoxycarbonyl- cyclopent-1-ene as an oil.

EXAMPLE 9

The fungicidal activity of compounds of the invention was investigated in specific screens and by means of the following tests.

(a) Antisporulant activity against vine downy mildew (Plasmopara viticola; Pva)

The test is a direct antisporulant one using a foliar spray. The lower surfaces of leaves of whole vine plants (cv Cabernet Sauvignon) are inoculated by spraying with an aqueous suspension containing $10^4$ zoosporangia/ml 2 days prior to treatment with the test compound. The inoculated plants are kept for 24 hours in a high humidity compartment, then 24 hours at glasshouse ambient temperature and humidity. Infected leaves are sprayed on their lower surfaces with a solution of active material in 1:1 water/acetone containing 0.04% "TWEEN 20" (Trade Mark; a polyoxyethylene sorbitan ester surfactant). The spraying is carried out with a moving track sprayer giving an application rate of 1 kg/ha. After spraying, the plants are returned to normal glasshouse conditions for 96 hours and are then transferred to the high humidity compartment for 24 hours to induce sporulation, prior to assessment. Assessment is based on the percentage of the leaf area covered by sporulation compared with that on control leaves.

(b) Direct protectant activity against vine downy mildew (Plasmopara viticola; Pvp)

The test is a direct protectant one using a foliar spray. The lower surfaces of leaves of whole vine plants (cv Cabernet Sauvignon) are sprayed with the test compound at a dosage of 1 kilogram of active material per hectare using a track sprayer as described under (a), and after a subsequent 24 hours under normal glasshouse conditions the lower surfaces of the leaves are inoculated by spraying with an aqueous solution containing $10^4$ zoosporangia/ml. The inoculated plants are kept for 24 hours in a high humidity compartment, 5 days under normal glasshouse conditions and then returned for a further 24 hours to high humidity. Assessment is based on the percentage of leaf area covered by sporulation compared with that on control leaves.

(c) Activity against barley powdery mildew (Erysiphe graminis f.sp. hordei; Eq)

The test is a direct therapeutic one, using a foliar spray. Leaves of barley seedlings, (cv. Golden Promise) are inoculated by dusting with mildew conidia one day prior to treatment with the test compound. The inoculated plants are kept overnight at glasshouse ambient temperature and humidity prior to treatment. The plants are sprayed with the test compound at a dosage of 1 kilogram of active material per hectare using a track sprayer as described under (a). After drying, plants are returned to a compartment at 20°-25° C. and moderate humidity for up to 7 days, followed by assessment. Assessment is based on the percentage of leaf area covered by sporulation compared with that on leaves of control plants.

(d) Activity against wheat brown rust (Puccinia recondita; Pr)

The test is a direct protectant one using a foliar spray. Wheat seedlings (cv Brigand) are grown to the 1–1½ leaf stage. The plants are then sprayed with the test compound at a dosage of 1 kg/ha using a track sprayer as described under (a). Test compounds are applied as solutions or suspensions in a mixture of acetone and water (50:50 v/v) containing 0.04% surfactant ("TWEEN 20" - Trade Mark).

18–24 hours after treatment, the seedlings are inoculated by spraying the plants from all sides with an aqueous spore suspension containing about $10^5$ spores/ml. For 18 hours after inoculation, the plants are kept in high humidity conditions at a temperature of 20°-22° C. Thereafter, the plants are kept in ambient glasshouse conditions, that is, in moderate relative humidity and at a temperature of 20° C.

The disease is assessed 10 days after inoculation on the basis of the percentage of the plant covered by sporulating pustules compared with that on the control plants.

(e) Activity against Fusarium in-vitro (Fusarium species; FsI)

This test measures the in vitro activity of compounds against a species of Fusarium that causes stem and root rots.

Compound is dissolved or suspended in acetone and added to molten half strength Potato Dextrose Agar to give a final concentration of 100 ppm compound and 3.5% acetone. After the agar has set, plates are inoculated with 6 mm diameter plugs of agar and mycelium taken from a 7 day old culture of Fusarium sp.

Plates are incubated at 20° C. for 5 days and radial growth from the plug is measured.

The extent of disease control in all the above tests is expressed as a rating compared with either an untreated control or a diluent-sprayed-control, according to the criteria:

0 = less than 50% disease control
1 = about 50–80% disease control
2 = greater than 80% disease control The results of these tests are set out in the Table below:

| Compound Example No. | Fungicidal Activity | | | | |
|---|---|---|---|---|---|
| | Pva | Pvp | Eg | Pr | FsI |
| 2 | 1 | 2 | 1 | 2 | |
| 4/6 | | | | | 1 |

I claim:
1. A compound of the formula I

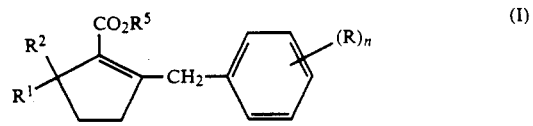

in which n represents an integer form 0 to 5; each R represents a halogen atom, nitro, cyano, hydroxyl, alkyl, haloalkyl, alkoxy, haloalkoxy, amino, alkylamino, dialkylamino, alkoxycarbonyl, carboxyl, alkanoyl, alkylthio, alkylsulphinyl, alkylsulphonyl, carbamoyl, alkylamido, cycloalkyl or phenyl group; $R^1$ an $R^2$ independently represent a hydrogen atom or an alkyl group; and $R^5$ represents a hydrogen atom or an alkyl or cycloalkyl group, with the proviso that, when n is 0 and $R^1$ and $R^2$ both represent a hydrogen atom, $R^5$ does not represent a hydrogen atom or a methyl group.

2. A compound of the formula II
in which n represents an integer form 0 to 5; each R represents a halogen atom, nitro, cyano, hydroxyl, $C_{1-12}$ alkyl, $C_{1-12}$ haloalkyl, alkoxy, haloalkoxy, amino, $C_{1-12}$ alkylamino, $C_{1-12}$ dialkylamino, alkoxycarbonyl, carboxyl, alkanoyl, $C_{1-12}$ alkylthio, $C_{1-12}$ alkylsulphinyl, $C_{1-12}$ alkylsulphonyl, carbamoyl, $C_{1-12}$ alkylamido, $C_{3-8}$ cycloalkyl or phenyl group; $R^1$ and $R^2$ independently represent a hydrogen atom or an $C_{1-12}$ alkyl group; and $R^5$ represents a hydrogen atom or a $C_{1-12}$ alkyl or $C_{1-12}$ cycloalkyl group.

3. A fungicidal composition which comprises a carrier and, as active ingredient, a compound of the formula

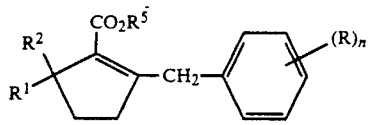

(I)

in which n represents an integer from 0 to 5; each R represents a halogen atom, nitro, cyano, hydroxyl, $C_{1-12}$ alkyl, $C_{1-12}$ haloalkyl, alkoxy, haloalkoxy, amino, $C_{1-12}$ alkylamino, $C_{1-12}$ dialkylamino, alkoxycarbonyl, carboxyl, alkanoyl, $C_{1-12}$ alkylthio, $C_{1-12}$ alkylsulphinyl, $C_{1-12}$ alkylsulphonyl, carbamoyl, $C_{1-12}$ alkylamido, $C_{3-8}$ cycloalkyl or phenyl group; $R^1$ and $R^2$ independently represent a hydrogen atom or an $C_{1-12}$ alkyl group; and $R^5$ represents a hydrogen atom or an $C_{1-12}$ alkyl or $C_{1-12}$ cycloalkyl group.

4. A fungicidal composition which comprises a carrier and, as active ingredient, a compound of the formula 5. A method of combating fungus at a locus which comprises treating the locus with a composition as defined in claim 3.

6. A method of combating fungus at a locus which comprises treating the locus with a composition as defined in claim 4.

* * * * *